United States Patent [19]

Stach

[11] Patent Number: 4,491,469
[45] Date of Patent: Jan. 1, 1985

[54] HERBICIDAL OXIME ESTERS OF 2-METHOXY-3,6-DICHLOROBENZOIC ACID

[75] Inventor: Leonard J. Stach, Riverside, Ill.

[73] Assignee: Velsicol Chemical Corporation, Chicago, Ill.

[21] Appl. No.: 470,110

[22] Filed: Feb. 28, 1983

[51] Int. Cl.³ .................... A01N 37/40; C07C 131/00
[52] U.S. Cl. .................................. 71/121; 564/254
[58] Field of Search .......................... 564/254; 71/121

[56] References Cited
U.S. PATENT DOCUMENTS
3,547,621 12/1970 Neighbors et al. .................. 71/121

Primary Examiner—Natalie Trousof
Assistant Examiner—L. Hendriksen
Attorney, Agent, or Firm—Robert J. Schwarz

[57] ABSTRACT

This application discloses compounds of the formula:

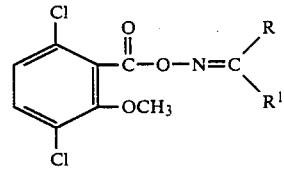

wherein R and R¹ are selected from alkyl and phenyl and can form a cyclic group having 5 or 6 carbon atoms.

The disclosed compounds are useful as herbicides.

8 Claims, No Drawings

HERBICIDAL OXIME ESTERS OF 2-METHOXY-3,6-DICHLOROBENZOIC ACID

This invention relates to new esters of 2-methoxy-3,6-dichlorobenzoic acid. In particular this invention relates to esters of dicamba having the following structural formula:

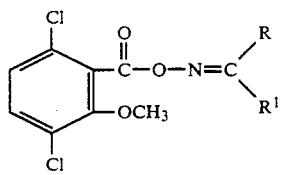

wherein R and $R^1$ are selected from alkyl and phenyl and can form a cyclic group having 5 or 6 carbon atoms. It is preferred that the alkyl have from one to six carbon atoms.

The compounds of the present invention can be prepared by reacting the acid chloride of 2-methoxy-3,6-dichlorobenzoic acid with an oxime. The selection of the oxime will depend upon the desired R and $R^1$ groups.

This reaction proceeds without heating at room and lower temperatures. The product can be used as it is obtained from the reaction mixture or it can be purified by standard procedures.

EXAMPLE 1

PREPARATION OF THE ACETONE OXIME ESTER Of 2-Methoxy-3,6-Dichlorobenzoic Acid Acetone oxime (14.6 grams; 0.20 moles), 3,5-lutidine (22 grams) and methylene chloride (200 ml) were placed into a three-necked, 500 ml, glass reaction flask equipped with mechanical stirrer, thermometer, condenser and addition funnel. 2-Methoxy-3,6-dichlorobenzoic acid chloride (47.8 grams; 0.20 moles) was added dropwise to the reaction mixture with the temperature maintained below 10° C. After the addition was completed, the reaction mixture was stirred for three hours at room temperature. Then the mixture was washed three times with water, dried over anhydrous magnesium sulfate, filtered and concentrated. The residue was crystallized from a mixture of toluene and hexane to give a white crystalline solid. Melting point = 43°–46° C.

Elemental Analysis:

|  | C (%) | H (%) | N (%) | Cl (%) |
| --- | --- | --- | --- | --- |
| Theoretical: | 47.85 | 4.02 | 5.07 | 25.68 |
| Found: | 48.06 | 4.05 | 5.09 | 25.43 |

EXAMPLE 2

PREPARATION OF THE BENZALDEHYDE OXIME ESTER OF 2-Methoxy-3,6-Dichlorobenzoic Acid Benzaldehyde Oxime (24.2 grams; 0.20 moles); 3,5-lutidine (22 grams) and methylene chloride (200 ml) are placed into a three-necked, 500 ml, glass reaction flask equipped with mechanical stirrer, thermometer, condenser and addition funnel. 2-Methoxy-3,6-Dichlorobenzoic Acid Chloride (47.8 grams; 0.20 moles) are added dropwise to the reaction mixture with the temperature maintained below 10° C. After the addition is complete, the reaction mixture is stirred for three (3) hours at room temperature. Then the mixture is washed with water, dried over anhydrous magnesium sulfate, filtered and concentrated. The residue is purified by crystallization.

EXAMPLE 3

PREPARATION OF THE CYCLOHEXANONE OXIME ESTER OF 2-Methoxy-3,6-Dichlorobenzoic Acid Cyclohexanone oxime (22.6 grams; 0.2 moles), 3,5-lutidine (22 grams) and methylene chloride (200 ml) are placed into a three-necked, 500 ml, glass reaction flask equipped with mechanical stirrer, thermometer, condenser and addition funnel. 2-Methoxy-3,6-Dichlorobenzoic Acid Chloride (47.8 grams; 0.20 moles) are added dropwise to the reaction mixture with the temperature maintained below 10° C. After the addition is complete, the reaction mixture is stirred for three (3) hours at room temperature. Then the mixture is washed with water, dried over anhydrous magnesium sulfate, filtered and concentrated. The residue is purified by crystallization.

Other compounds within the scope of this invention which can be prepared by the aforedescribed procedure are:

diethyl ketone oxime esters of 2-methoxy-3,6-dichlorobenzoic acid, dipropyl ketone oxime ester of 2-methoxy-3,6-dichlorobenzoic acid, methyl butyl ketone oxime ester of 2-methoxy-3,6-dichlorobenzoic acid, ethyl propyl ketone oxime ester of 2-methoxy-3,6-dichlorobenzoic acid, benzophenoneoxime ester of 2-methoxy-3,6-dichlorobenzoic acid, cyclohexane oxime ester of 2-methoxy-3,6-dichlorobenzoic acid.

For practical use as herbicides, the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules or wettable powders; or they can be liquids such as solutions, aerosols or emulsifiable concentrates.

For example, dusts can be prepared by grinding and blending the active compound with a solid inert carrier such as the talcs, clay silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders which can be dispersed in water or oil to any desired concentration of the active compound can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestation.

A typical herbicidal composition according to this invention is illustrated by the following example in which the quantities are in parts by weight.

EXAMPLE 4

PREPARATION OF A DUST

| Product of Example 1 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and, as an essential active ingredient in a quantity which is herbicidally toxic to said weeds, a compound of the present invention. The concentration of the new compounds of this invention in the herbicidal compositions will vary greatly with the type of formulation and the purpose for which it is designed, but generally the herbicidal composition will comprise from about 0.5 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions of the individual herbicides. The other herbicides, defoliants, dessicants and the plant growth inhibitors, with which the compounds of this invention can be used in the herbicidal composition to control weeds, can include chlorophenoxy herbicides such as 2,4-D, 2,4,5-T, MCPA, MCPB, 4(2,4-DB), 2,4-DEB, 4-CPB, 4-XPP, 2,4,5-TB, 2,4,5-TES, 3,4-DA, silvex and the like; carbamate herbicides such as IPC, CIPC, swep, barban, BCPC, CEPC, CPPC and the like; thiocarbamate and dithiocarbamate herbicides such as DCEC, methan sodium, EPTC, diallate, PEBC, perbulate, vernolate and the like; substituted urea herbicides such as norea, disuron, dichloral urea, chloroxuron, cycluron, fenuron, monuron, monuron TCA, diuron, linuron, molinuron, neburon, buturon, trimeturon and the like; symmetrical triazine herbicides such as simazine, chlorazine, atraone, desmetryne, norazine, ipazine, prometryn atrazine, trietazine, simetone, prometone, propazine, ametryne and the like; chloroacetamide herbicides such as alpha-chloro-N,n-dimethylacetamide, CDEA, CDAA, alpha-chloro-N-isopropylacetamide, 2-chloro-N-isopropyl-acetanilide, 4-(chloroacetyl)-morpholine, 1-(chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamide, dipropalin, triduraline, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, iosynil, IPX, isocril, potassium cyanate, MAA, MAMA, MCPES, MCPP, MH, molinate, NPA, OCH paraquat, PCP, picloram, DPA, PCA, pyrichlor, sesone, terbacil, terbutol, TCBA, brominil, CP-50144, H-176-1, H-732, M-2091, planavin, dosium, tetraborate, calcium cyanamid, DEF, ethyl xanthogen disulfide, sindone, sindone B, propanil and the like.

Such herbicides can also be used in the methods and composition of this invention in the form of their salts, esters, amides and other derivatives whenever applicable to the particular patent compound.

Weeds are undesirable plants growing where they are not wanted, having no economical value and interfering with the production of cultivated crops, with the growing of ornamental plants or with the welfare of livestock. Many types of weeds are known, including annuals such as pigweed, lambs-quarter, foxtail, crabgrass, wild mustard, field pennycress, ryegrass, goose grass, chickweed, wild oats, velvet leaf, purselane, barnyard grass, smartweed, knotweed, cocklebut, wild buckwheat, kochia, medic corn cockle, ragweed, sowthistle, coffee-weed, croton, cupheah, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein and purple star thistle; or perennials such as white cockle, perennial rye-grass, quack grass, Johnson grass, Canada thistle, hedge bindweed, Bermuda grass, sheep sorrel, curly dock, nutgrass, field chickweed, dandelion, campanula, field bindweed, Russian knapweed, mewquite, toadflax, yarrow, aster, gromwell, horsetail, ironweed, sesbania, bulrush, cattail and wintercrass.

Similarly, such weeds can be classified as broadleaf or grassy weeds. It is economically desirable to control the growth of such weeds without damaging beneficial plants of livestock.

The new compounds of this invention are particularly valuable for weed control because they are toxic to many species and groups of weeds they are relatively non-toxic to many beneficial plants. The exact amount of compound required will depend on a variety of factors, including the hardiness of the particular weed species, weather, type of soil, method of application, the kind of beneficial plants in the same area and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compound formulated as aqueous emulsions of acetone solutions containing emulsifiers was sprayed at the indicated concentrations on the surface of the soil.

After spraying, the soil containers were placed in the greenhouse and provided with supplementary heat as required and daily or more frequently watering. The plants were maintained under these conditions for a period of from 14 to 21 days, at which time the condition of the plants and the degrees of injury of the plants were rated on a scale of from 0 to 10 as follows: 0=no injury; 1,2=slight injury; 3,4=moderate injury; 5,6=moderately severe injury; 7,8, 9=severe injury and 10=death. The effectiveness of the compound of Example 1 is demonstrated by the following data:

| PRE-EMERGENCE HERBICIDE TEST DATA 14 DAYS AFTER TREATMENT | | | | |
|---|---|---|---|---|
| RATE OF APPLICATION | 0.25 | 0.125 | 0.062 | 0.031 |
| Jimsonweed | 7 | 4 | 4 | 0 |
| Velvet Leaf | 7 | 5 | 3 | 2 |
| Pigweed | NE | 2 | 2 | 0 |
| Wild Mustard | NE | 0 | 0 | 4 |
| Morning Glory | 7 | 6 | 6 | 0 |
| Wild Oats | 1 | 0 | 0 | 0 |
| Johnson Grass | 5 | 0 | 0 | 0 |
| Yellow Foxtail | 9 | 0 | 0 | 0 |
| Barnyard Grass | 8 | 0 | 0 | 0 |
| Crabgrass | 0 | 0 | 0 | 0 |
| Cheat Grass | 2 | 0 | 0 | 0 |
| Yellow Nutsedge | 0 | 0 | 0 | 0 |

| PRE-EMERGENCE HERBICIDE TEST DATA 21 DAYS AFTER TREATMENT | | | | |
|---|---|---|---|---|
| RATE OF APPLICATION (Pounds Per Acre) | 0.25 | 0.125 | 0.062 | 0.031 |
| Jimsonweed | 8 | 1 | 4 | 0 |
| Velvet Leaf | 8 | 4 | 3 | 3 |
| Pigweed | NE | 3 | 2 | 0 |
| Wild Mustard | NE | 3 | 1 | 3 |
| Morning Glory | 7 | 4 | 4 | 0 |
| Wild Oats | 2 | 0 | 0 | 0 |
| Johnson Grass | 2 | 0 | 0 | 0 |
| Yellow Foxtail | 8 | 0 | 0 | 0 |
| Barnyard Grass | 7 | 0 | 0 | 0 |
| Crabgrass | 0 | 0 | 0 | 0 |
| Cheat Grass | 2 | 0 | 0 | 0 |
| Yellow Nutsedge | 0 | 0 | 0 | 0 |

The herbicidal activity of the compounds of this invention was also demonstrated by experiments carried out for the post-emergence control of a variety of weeds. In these experiments the compound to be tested was formulated as aqueous emulsions and sprayed at a dosage of 0.25 pound per acre on the foliage of the various weed species that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretobefore described. The effectiveness of these compounds is demonstrated by the following data:

| Bindweed | 4 |
|---|---|
| Jimsonweed | 7 |
| Pigweed | 6 |
| Wild Mustard | 5 |
| Morning Glory | 7 |
| Wild Oats | 2 |
| Johnson Grass | 0 |
| Yellow Foxtail | 3 |
| Barnyard Grass | 0 |
| Crabgrass | 2 |
| Yellow Nutsedge | 0 |
| Soybeans | 10 |

I claim:
1. A compound of the formula:

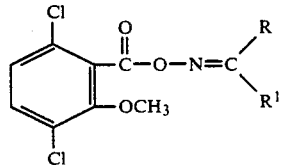

wherein R and R$^1$ are selected from alkyl and phenyl and R$_1$ and R$_2$ together can form a cyclic group having 5 or 6 carbon atoms.

2. The compound of claim 1 wherein R and R$^1$ are independently selected from alkyl having up to 6 carbon atoms.

3. The compound of claim 1, acetone oxime ester of 2-methoxy-3,6-dichlorobenzoic acid.

4. The compound of claim 1, diethyl ketone oxime ester of 2-methoxy-3,6-dichlorobenzoic acid.

5. The compound of claim 1, methyl butyl ketone oxime ester of 2-methoxy-3,6-dichlorobenzoic acid.

6. The compound of claim 1, cyclohexanone oxime ester of 2-methoxy-3,6-dichlorobenzoic acid.

7. A herbicidal composition comprising an inert carrier and, as an essential ingredient in a quantity toxic to weeds, a compound of claim 1.

8. A method of controlling weeds which comprises contacting said weeds with the herbicidal composition of claim 1.

* * * * *